United States Patent [19]
Mack

[11] Patent Number: 6,086,530
[45] Date of Patent: Jul. 11, 2000

[54] ADJUSTABLE SLEEVE FOR ENDOSCOPES

[76] Inventor: Michael Mack, 7 Argyle Rd., Rye Brook, N.Y. 10573

[21] Appl. No.: 09/183,373

[22] Filed: Oct. 30, 1998

[51] Int. Cl.[7] .......................................................... A61B 1/00
[52] U.S. Cl. .......................... 600/121; 600/123; 600/125
[58] Field of Search .................................... 600/104, 121, 600/123, 124, 125, 127, 136, 137, 138; 606/45, 46

[56] References Cited

U.S. PATENT DOCUMENTS

| | | |
|---|---|---|
| 3,643,653 | 2/1972 | Takahashi et al. . |
| 4,188,942 | 2/1980 | Fehlberg . |
| 4,254,762 | 3/1981 | Yoon . |
| 4,972,827 | 11/1990 | Kishi et al. . |
| 5,329,935 | 7/1994 | Takahashi . |
| 5,359,991 | 11/1994 | Takahashi . |
| 5,400,770 | 3/1995 | Nakao et al. . |
| 5,495,286 | 2/1996 | Adair ........................................... 348/68 |
| 5,681,262 | 10/1997 | Isse ........................................... 600/127 |
| 5,692,506 | 12/1997 | Linder ........................................ 128/642 |
| 5,695,449 | 12/1997 | Moriyama . |
| 5,885,258 | 3/1999 | Sachdeva et al. ........................ 604/281 |

OTHER PUBLICATIONS

Olympus Brochure—"Endoscopic plastic surgery instruments for aesthetic and reconstructive surgery".
Richard Wolf Medical Instruments Corp.—"Endoscopic Sinus Surgery".

*Primary Examiner*—Linda C. M. Dvorak
*Assistant Examiner*—Brad C. Blaise
*Attorney, Agent, or Firm*—Thomas K. Landry, Esq.

[57] ABSTRACT

A sleeve for medical instruments such as endoscopes is disclosed. The sleeve is attachable in any axial or rotational orientation on the endoscope tube. A clamp-like locking means holds the sleeve securely to the endoscope tube without causing damage, while a locking screw permits easy locking, releasing or adjustment. A flared extension at the distal end of the sleeve facilitates stabilization during medical procedures.

8 Claims, 2 Drawing Sheets

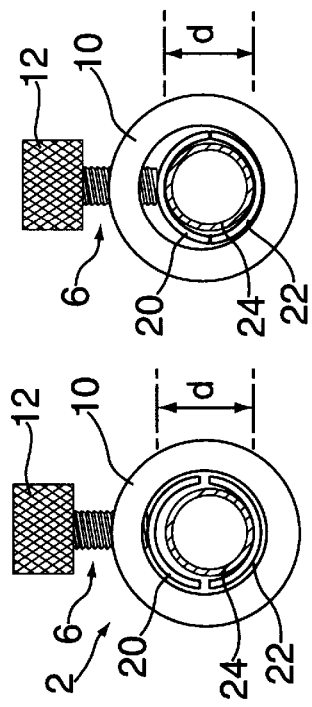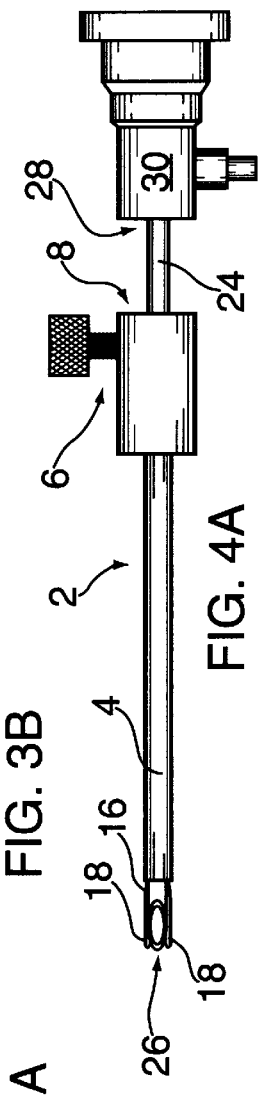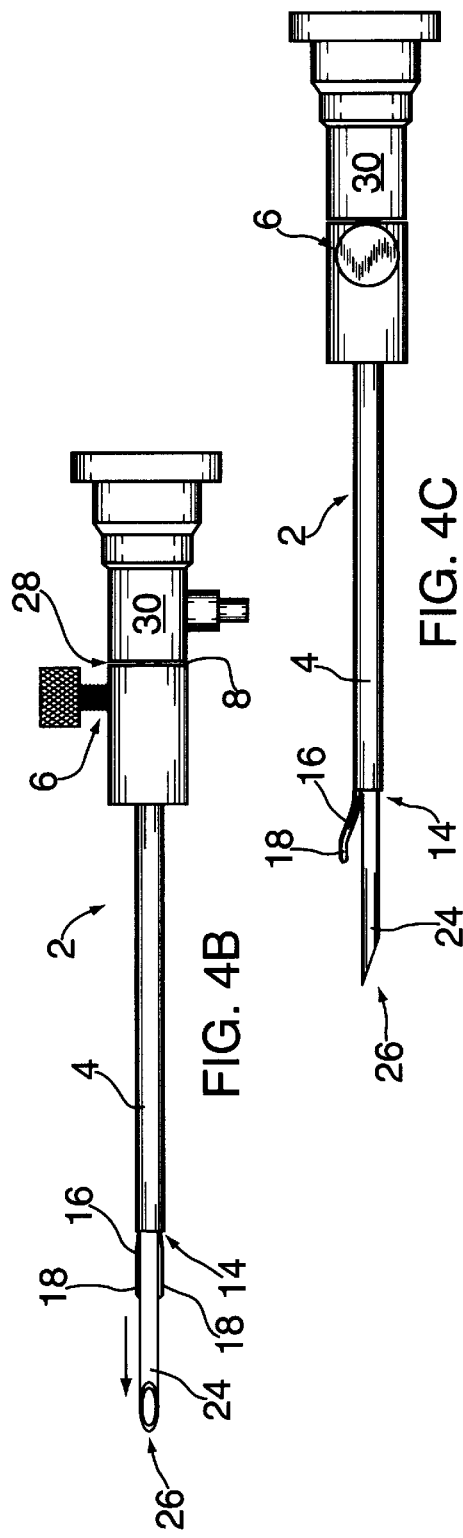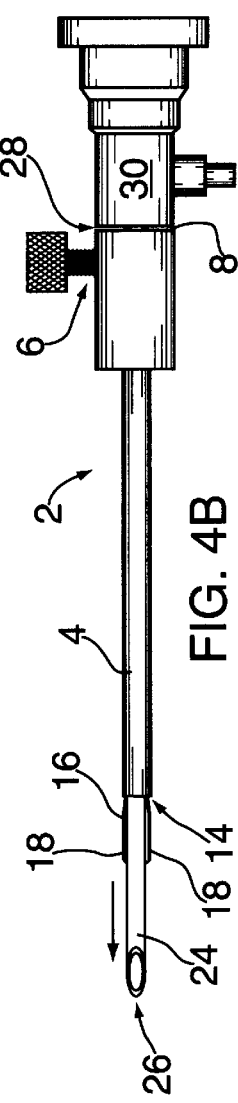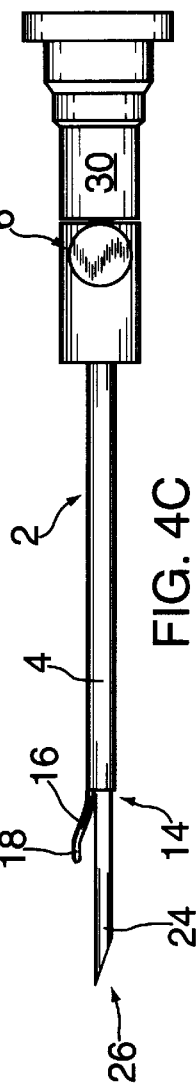

ADJUSTABLE SLEEVE FOR ENDOSCOPES

FIELD OF THE INVENTION

This invention concerns a sleeve for medical instruments such as endoscopes. The invention is especially useful for dental and other procedures in which it is desirable to stabilize an endoscope while allowing repeated positional adjustment.

BACKGROUND OF THE INVENTION

An endoscope is a long, thin instrument used in medical procedures to view or operate inside a patient's body with minimal intrusiveness. Rather than opening a large cavity to reach a location in a patient's body, a doctor can create a small opening and reach the location by inserting and guiding the endoscope. To view inside a body, the distal end of the endoscope is mounted with a camera lens that transmits a video image of the surrounding tissue. The lens is often cut at an angle to yield an image of the tissue that is more or less (depending on the angle) to the side of, rather than directly in front of, the end of the endoscope.

Endoscopes can be rigid or flexible. A rigid endoscope is in the form of a long, thin tube connected to a base joint, which in turn is typically mounted on a handle. A flexible endoscope is in the form of a long, thin cable. The present invention is for use with rigid endoscopes.

A rigid endoscope is usually fitted with a sleeve: a hollow, rigid tube into which the endoscope is inserted, of a length slightly less than that of the endoscope. The shorter length of the sleeve permits the distal end of the endoscope to protrude slightly from the distal end of the sleeve, thus enabling the imaging or other function of the endoscope. Particularly when the endoscope has an angled lens for viewing sideways, the sleeve may end in an angled cut or an irregular cutaway shape to cover the endoscope as much as possible while permitting the lens to view its object. Prior sleeves connect to the endoscope at the proximal end (i.e., the end nearer to the base joint) and are immovably fixed in relation to the endoscope.

An endoscope sleeve may perform various purposes. One purpose is to protect the endoscope as it is pushed, pulled, and angled within a patient. Another purpose is to introduce irrigation or suction to the area surrounding the distal end, thus either flushing the area with an externally supplied fluid or removing internal matter from the area. For either purpose, the inner diameter of the sleeve is of sufficiently greater diameter than the outer diameter of the endoscope to form a space, or channel, between the two tubes. Irrigation or suction is introduced through that space or channel.

Another purpose of an endoscope sleeve can be to spread bodily tissue away from the distal end of the endoscope, thus clearing a space for the imaging or other function. To this end, the distal end of the sleeve may terminate in a flared tip that angles outwardly from the tubular sleeve. The flared tip pushes or lifts tissue away from the axis of the sleeved endoscope, sheltering the distal end of the endoscope in an umbrella-like space.

Prior sleeves for rigid endoscopes pose several problems for their users. First, the sleeves are sometimes difficult to stabilize in the area to be viewed or treated. Instability compromises the quality and accuracy of the imaging or other function being performed. It is sometimes possible to anchor the endoscope sleeve on nearby tissue; because the endoscope is fixed to the sleeve, the endoscope is stabilized. But such a technique depends on coincidence. Anchoring the sleeve in a convenient spot will not necessarily leave the distal end of the endoscope in its required location.

Second, even if the sleeve could be anchored in a spot that placed the distal end of the endoscope in a favorable position, it would usually be necessary to move the endoscope in various directions—pushing, pulling, rotating, angling—with the result that the anchoring spot for the sleeve would soon be lost. The sleeve simply cannot remain anchored while the endoscope is moved, because the two are fixed relative to one another.

Third, an endoscope fixed to a sleeve is bulkier than an endoscope alone, which limits the spaces into which the endoscope may reach. This is of particular concern where the instrument must pass through a small opening in solid material like bone.

It is therefore an object of this invention to provide an endoscope sleeve that facilitates stabilization of an endoscope to which the sleeve is attached.

It is another object of this invention to provide an endoscope sleeve that permits axial and rotational movement of the endoscope relative to the sleeve.

It is a further object of this invention to provide an endoscope sleeve that can be fixed to an endoscope selectively along the endoscope's length and circumference.

It is yet another object of this invention to provide an endoscope sleeve that operates as an effective anchor when positioned against a stable surface.

It is still another object of this invention to provide an endoscope sleeve that permits extension of the distal end of the endoscope substantially beyond the distal end of the sleeve, thus facilitating the examination of spaces unreachable by a combined endoscope and sleeve.

SUMMARY OF THE INVENTION

The present invention provides an endoscope sleeve that can be fixed at any point along the length of, and in any radial orientation around the circumference of, an endoscope. A clamp-like locking means at the proximal end of the sleeve engages the outer surface of the endoscope and holds the two parts together. This is preferably accomplished by means of a screw that threads through a collar around the proximal end of the sleeve and tightens a portion of the sleeve against the endoscope. The sleeve tube is preferably slotted to permit displacement of a section of the tube wall toward and away from the endoscope. The greater the surface area of the displaced section of the tube wall, the more widely distributed the pressure on the endoscope will be. A wider distribution of pressure reduces the possibility of damage to the endoscope.

If the length of the sleeve is shorter than the endoscope, then the endoscope can be extended beyond the end of the sleeve and reach locations that could not be reached if the sleeve, which is wider than the endoscope, covered the entire length of the endoscope.

The sleeve has a flared extension at its distal end to facilitate stabilizing the sleeve and endoscope during a medical procedure. The flared extension could be a separate element attached to the sleeve but preferably is a contiguous extension of part of the circumference of the tube portion of the sleeve. The extension is anchored on a surface near the area where the endoscope is to be used. Although it is not necessary that the extension flare outwardly from the sleeve tube, a flared construction puts a small distance between the extension and the endoscope and provides greater flexibility in anchoring the sleeve.

The flared extension is particularly useful when the sleeve is shorter than the endoscope. In dental procedures, for example, such a sleeve can be anchored on the top or side of a tooth while the endoscope extends into a drilled opening. Not only is the instrument thus more stable, the drilling or incision need not be as wide as if the sleeve covered the length of the endoscope.

The clamp lock between the sleeve and endoscope can be loosened at any time for adjustment of the endoscope's position without disturbing the anchored position of the sleeve. Alternatively, the clamp lock on the sleeve can be left disengaged from the endoscope, with the sleeve used simply to guide the position of the endoscope. This would be particularly useful if the sleeve were anchored in a favorable spot but considerable movement of the endoscope were required.

Many endoscope sleeves facilitate irrigation or suction through a channel between the endoscope and the sleeve. Those functions are possible with the present sleeve invention, provided that it is equipped with certain additional features. Because the proximal end of the sleeve does not connect to the base joint of the endoscope but instead is selectively fixed along the length of the endoscope, it is necessary to provide a conduit between the base joint of the endoscope and the proximal end of the sleeve, and further necessary to provide a seal around the proximal end of the sleeve to prevent leakage from the irrigation or suction channel. The conduit is preferably a flexible tubing of sufficient length and flexibility to allow the full range of axial and rotational adjustment that the sleeve enables. The seal is preferably of sufficient quality and construction to provide effective protection against leakage but not impair the ability of a user to smoothly adjust the sleeve's axial or rotational position.

BRIEF DESCRIPTION OF THE DRAWINGS

In the accompanying drawings which form a part of this specification:

FIG. 3A is an elevation end view of the proximal end of the endoscope sleeve of the invention, mounted on an endoscope (shown in cross-section), with the sleeve's clamp-like locking means disengaged;

FIG. 3B is an elevation end view of the proximal end of the endoscope sleeve of the invention, mounted on an endoscope (shown in cross-section), with the sleeve's clamp-like locking means engaged;

FIG. 4A is an elevation side view of the endoscope sleeve of the invention, mounted on an endoscope and positioned with the distal end of the sleeve aligned with the distal end of the endoscope;

FIG. 4B is an elevation side view of the endoscope sleeve of the invention, mounted on an endoscope and positioned with the proximal end of the sleeve aligned with the proximal end of the endoscope;

FIG. 4C is an elevation top view of the endoscope sleeve of the invention, mounted on an endoscope and positioned with the proximal end of the sleeve aligned with the proximal end of the endoscope.

DETAILED DESCRIPTION OF THE PREFERRED EMBODIMENTS

Figure 1A:
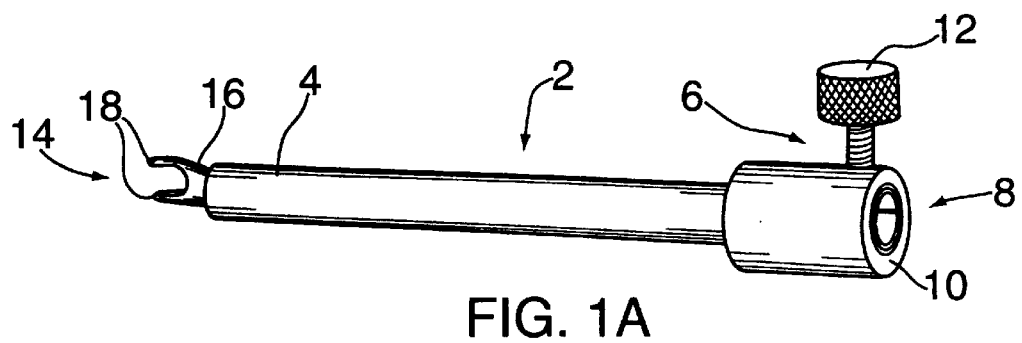
FIG. 1A is a perspective side view of the endoscope sleeve of the invention, having a forked stabilizer extension.

In the accompanying drawing FIG. 1A, the endoscope sleeve 2 of the present invention is shown unattached to an endoscope. The sleeve 2 has a sleeve tube 4 with clamp-like locking means 6 at the sleeve's proximal end 8. Clamp lock 6 comprises a collar 10 into which a locking screw 12 is threaded. Locking screw 12, when tightened into the collar 10, engages the outside of the sleeve tube 4 at the proximal end 8. The sleeve tube 4 is slotted at that end, and the engagement of locking screw 12 forces the slotted sections of sleeve tube 4 together, enabling them to lock the sleeve to an endoscope on which the invention has been mounted.

Figure 1B:
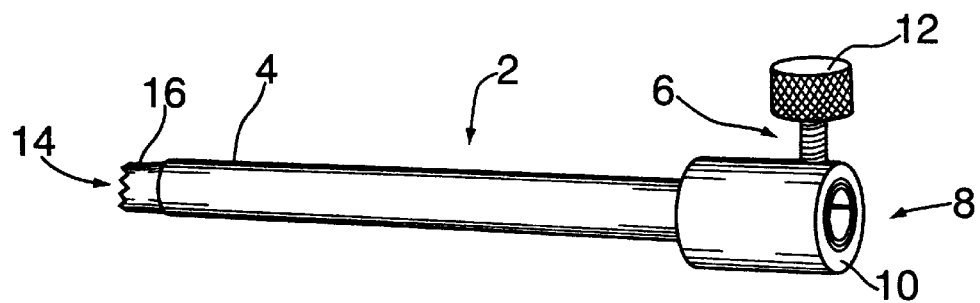
FIG. 1B is a perspective side view of the endoscope sleeve of the invention, having a serrated stabilizer extension.

The distal end 14 of sleeve 2 has a flared extension 16 for stabilization. The preferred design of extension 16 depends on the surface on which the extension is to be anchored. In FIG. 1A, the extension 16 has a forked design that is especially useful for dental applications. Tines 18 of the extension 16 are easily and effectively positioned across, or on top of, a dental patient's teeth. In FIG. 1B, the extension 16 has a serrated design. Other designs may be desirable as well, depending on the location and manner in which an endoscope is to be used.

Figure 1C:
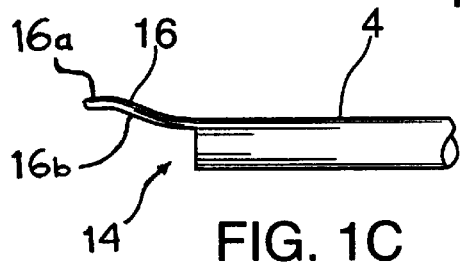
FIG. 1C is a cut-off side view of the endoscope sleeve of the invention, showing the flared construction of the stabilizer extension.

In FIG. 1C, extension 16 is shown to have a flared structure in relation to the sleeve tube 4. Extension 16 nonetheless extends contiguously from part of the circumference of sleeve tube 4. Extension 16 comprises an angled segment 16a that flares extension 16 outwardly from the axis and circumference of sleeve tube 4, and a stabilizing extension segment 16b that extends parallel to sleeve tube 4 and beyond the distal end 14 of sleeve tube 4. The structure of extension 16 thus provides a stabilizer or anchor that, relative to the axis of sleeve tube 4, is positioned outside the circumference of sleeve tube 4, thereby facilitating not only stabilization of the endoscope and sleeve but ample work space and freedom of movement for the endoscope beyond distal end 14 of the sleeve. This structure is further depicted in, and described in connection with, FIG. 4C.

Figure 2:
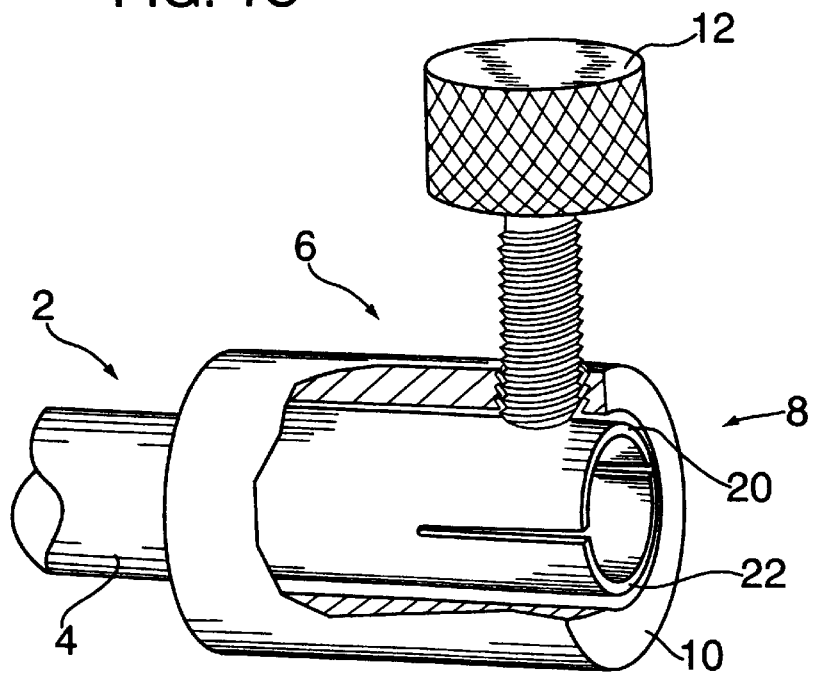
FIG. 2 is a cut-away view of the clamp-like locking means at the proximal end of the endoscope sleeve of the invention.

In FIG. 2, clamp lock 6 at the proximal end 8 of the sleeve 2 is shown to comprise collar 10 mounted on sleeve tube 4, with locking screw 12 threaded through collar 10. Sleeve tube 4 is slotted at proximal end 8 of sleeve 2, thus defining slotted sections 20 and 22. Collar 10 is welded to slotted section 22, and may also be welded to sleeve tube 4 beyond slotted sections 20 and 22. Collar 10 is not, however, welded to slotted section 20, which leaves slotted section 20 free to be displaced toward and away from slotted section 22. Tightening locking screw 12 into engagement with slotted section 20 forces that section toward slotted section 22. An endoscope passed through sleeve tube 4 would be locked between the compressed slotted sections 20 and 22, which act as pressure plates against the endoscope.

The operation of clamp lock 6 is further depicted in FIGS. 3A and 3B. In FIG. 3A, the sleeve 2 is mounted on an endoscope tube 24. Locking screw 12, through collar 10, just barely engages slotted section 20 opposite slotted section 22. In such a state, endoscope tube 24 is free to move axially or rotationally within sleeve 2. This state may be preferred when substantial or frequent adjustment of the position of endoscope tube 24 will be necessary. In such instances, sleeve 2 functions as a guide to the movements of the endoscope and as a shield protecting the endoscope's surface.

In FIG. 3B, locking screw 12, in collar 10, is fully engaged with slotted section 20 opposite slotted section 22, and slotted sections 20 and 22 are compressed against endoscope tube 24. Sleeve 2 is thus fixed to endoscope tube 24. Although a rigid endoscope is a fragile instrument because of its long, thin tube, and although the present invention is locked to that fragile section of an endoscope, the preferred structure of the present invention as shown in the accompanying drawings assures that damage to an endoscope will be avoided. Specifically, the pressure of sections 20 and 22 against endoscope tube 24 is spread over the surface area of sections 20 and 22, thus preventing concentrated forces from damaging endoscope tube 24.

In FIG. 4A, the sleeve 2 is mounted on an endoscope tube 24, with the sleeve 2 positioned just about as far toward the distal end 26 of the endoscope tube 24 as would be practicable without impeding the function of the endoscope. (If the sleeve were positioned much further toward the distal end of the endoscope tube, the sleeve tube 4 of the sleeve would cover the distal end 26 of the endoscope tube and block the endoscope from functioning.) Likewise, the distance between the proximal end 8 of the sleeve 2 and the proximal end 28 of the endoscope tube is just about the greatest it can be without impeding the function of the endoscope. Tines 18 of flared extension 16 are visible behind distal end 26 of the endoseope. Base joint 30 connects the endoscope tube 24 to remote equipment for such purposes as video display or recording.

In FIG. 4B, the sleeve 2 is positioned just about as far toward the proximal end 28 of the endoscope tube 24 as possible, with proximal end 8 of the sleeve 2 nearly abutting proximal end 28 of the endoscope tube 24. With the sleeve in this position, the distal end 26 of the endoscope tube 24 extends substantially beyond the distal end 14 of the sleeve tube 4. The endoscope tube 24, which of course is thinner than the sleeve tube 4, can therefore reach spaces that could not be reached if the sleeve tube 4 covered the entire length of endoscope tube 24. Tines 18 of flared extension 16 are visible behind the endoscope tube 24.

In FIG. 4C, the sleeve 2 is in the same position as in FIG. 4B, but is seen from above instead of from the side. As in FIG. 4B, the distal end 26 of the endoscope tube 24 extends substantially beyond the distal end 14 of the sleeve tube 4. Tines 18 of flared extension 16 are spaced from the endoscope tube 24 and are available to be anchored on any accessible, stable surface.

The endoscope sleeve of the present invention, as it is depicted in FIGS. 4A through 4C, may be either locked in place by engagement of clamp lock 6 or unlocked by disengagement of clamp lock 6. Whether the endoscope sleeve is locked depends on the medical application at hand. Some applications require substantial and frequent adjustment of the endoscope, in which case it may be preferable to leave the device unlocked and simply use the sleeve as a guide and anchor. Separate manipulation of the sleeve and endoscope would then be required to maintain positional control of each. If the endoscope were to be held steady, the locked state would usually be preferable because separate manipulation would be unnecessary. Often a successive combination of unlocked and locked states will be most desirable. Thus, a user may wish to: introduce the sleeve and endoscope to an area in the unlocked state; position the endoscope where it is to operate; anchor the sleeve's flared extension on the most stable accessible surface that the flared extension can contact; finally adjust the endoscope's position; lock the sleeve and endoscope; and if and when necessary, loosen the lock, adjust the endoscope's position, and re-tighten the lock.

According to an alternative embodiment of the invention, it is possible to introduce irrigation or suction through a channel between the endoscope tube 24 and the sleeve tube 4. Base joint 30 would be provided with a socket that is in communication with an external source of irrigation or suction. Proximal end 8 of the sleeve would be provided with a socket that is in communication with the channel between the endoscope tube 24 and the sleeve tube 4. A flexible tube would connect each of the sockets. A seal at proximal end 8 of the sleeve would prevent leakage while permitting axial and rotational movement of the sleeve relative to the endoscope tube 24.

The invention is preferably constructed entirely of surgical stainless steel, but various other materials, including but not limited to plastic or chrome-plated brass, could be used.

While the invention has been described by reference to illustrative embodiments, it is not intended that the novel device be limited thereby, but that modifications thereof are intended to be included as falling within the broad spirit and scope of the foregoing disclosure, the following claims and the appended drawings.

I claim:

1. A medical-instrument sleeve comprising: a hollow tube; a stabilizing extension extending beyond an axial end of said hollow tube, said stabilizing extension comprising a circumferential section of said hollow tube, said circumferential section comprising a forked stabilizing anchor; and means for clamping said tube to the medical instrument.

2. A medical instrument sleeve comprising: a hollow tube having a flared stabilizing extension, said stabilizing extension comprising a circumferential section of said hollow tube extending beyond an axial, distal end of said hollow tube, said circumferential section of said hollow tube comprising a forked stabilizing anchor and being flared outwardly and away from the axis of said hollow tube; and means for clamping said tube to the medical instrument, said clamping means comprising a slotted section of said hollow tube at one end of said hollow tube, a collar around said slotted section, and a screw through said collar.

3. A medical-instrument sleeve comprising: a hollow tube; and a stabilizing extension contiguous with said hollow tube, said extension having an angled segment and a stabilizing segment, said angled segment flaring said extension outwardly from the axis and circumference of the tube, and said stabilizing segment extending parallel to, and beyond a distal end of, the tube.

4. The medical-instrument sleeve of claim 3 wherein said stabilizing segment comprises a forked stabilizing anchor.

5. The medical-instrument sleeve of claim 4 further comprising means for clamping said sleeve at a selectable location on the medical instrument.

6. The medical-instrument sleeve of claim 3 wherein said stabilizing segment comprises a serrated stabilizing anchor.

7. The medical-instrument sleeve of claim 6 further comprising means for clamping said sleeve at a selectable location on the medical instrument.

8. The medical-instrument sleeve of claim 3 further comprising means for clamping said sleeve at a selectable location on the medical instrument.

* * * * *